000# United States Patent [19]
Volpin et al.

[11] 3,974,095
[45] Aug. 10, 1976

[54] CATALYST FOR HYDROGENATION, ISOMERIZATION AND HYDROSILYLATION OF ALKANES, AND METHOD OF PREPARATION

[75] Inventors: Mark Afimovič Volpin, Moscow, U.S.S.R.; Jiří Hetflejš, Prague, Czechoslovakia; Igor Sergeevič Kolomnikov, Moscow, U.S.S.R.; Petr Svoboda, Prague, Czechoslovakia; Vladimír Alexandrövič Sergeev, Moscow, U.S.S.R.; Valentin Kuzmič Sitikov, Moscow, U.S.S.R.

[73] Assignees: Ceskoslovenska akademie ved, Prague, Czechoslovakia; Akademie Nauk SSSR, Moscow, U.S.S.R.

[22] Filed: Dec. 19, 1974

[21] Appl. No.: 534,440

[30] Foreign Application Priority Data
Dec. 20, 1973  Czechoslovakia ................. 8856-73

[52] U.S. Cl. ..................... 252/429 R; 252/429 B; 252/430
[51] Int. Cl.$^2$ ........................................ B01J 31/02
[58] Field of Search ............ 252/429 A, 429 B, 430, 252/429 R

[56] References Cited
UNITED STATES PATENTS
3,493,343   2/1970   Logan et al. ..................... 252/430

*Primary Examiner*—J. Poer

[57] ABSTRACT

A catalyst for hydrogenation, isomeration and hydrosilylation of alkenes employes, as a polymeric supporting material, polyphenylene with a catalytically active metal (e.g., rhodium, ruthenium, palladium or platinum) deposited thereon.

6 Claims, 1 Drawing Figure

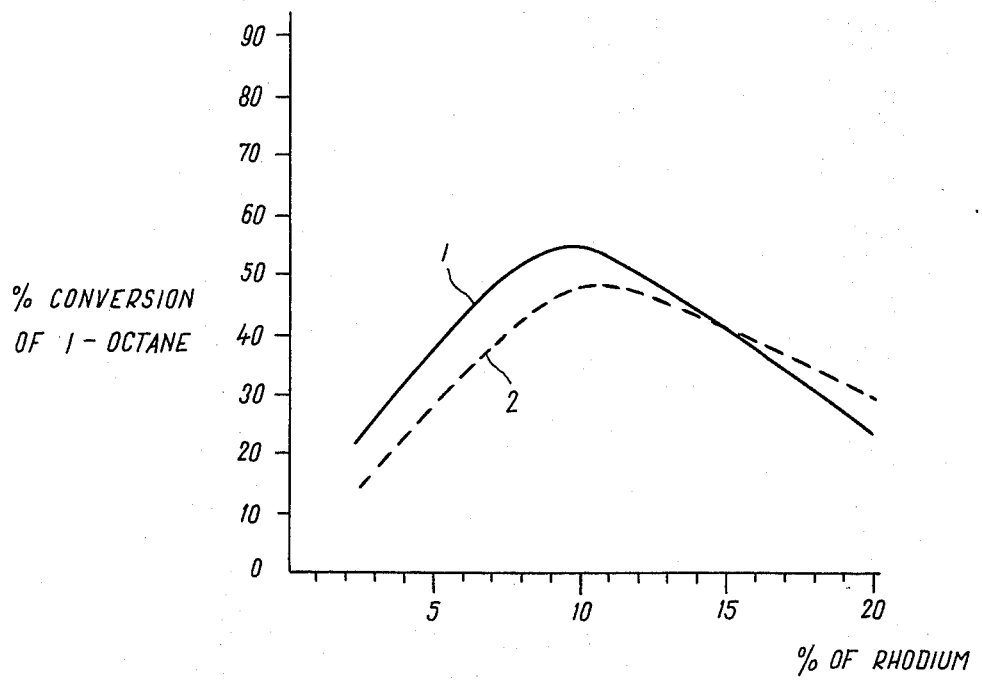

CATALYST FOR HYDROGENATION, ISOMERIZATION AND HYDROSILYLATION OF ALKANES, AND METHOD OF PREPARATION

BACKGROUND OF THE INVENTION

The invention relates to a catalyst for hydrogenation, isomerization and hydrosilylation of alkenes having 2–16 carbon atoms in the molecule, and to a manufacturing method for this catalyst.

Intensive work has been devoted to the preparation of catalysts deposited on polymeric supporting materials (i.e. ligants). Catalysts useful for hydrogenation and other reactions employ so-called π-complexes of transition metals, which complexes have utilized as ligants macrocyclical molecules of the aromatic type such as graphite. Complexes of phosphine ligants have also been advantageously used in catalytic processes.

It is also known that effective catalytic reactions of this type can be obtained (particularly in the heterogeneous phase) not only with the π-complexes themselves, but also with soluble analogs thereof. However, up to now an economical, readily accessible ligant useful in the production of both π-complexes and their analogs for particular uses (e.g., in the hydrogenation, isomerization and hydrosilylation of alkenes) has not been forthcoming. It would be further desirable to obtain a ligant of this type which is effective in the production of complexes both in the form of solutions and in the solid state.

SUMMARY OF THE INVENTION

An improved catalyst which exhibits all of the above-identified properties is provided by the present invention. In particular, the catalyst involves a ligant in the form of polyphenylene having a molecular specific weight higher than 1.000, with a catalytically active metal selected from the group consisting of palladium, platinum, rhodium and ruthenium deposited thereon in an amount of 0.5 to 20 percent by weight.

Such polyphenylene complexes of transistion metals can be applied both in a solid state and as a solution. Moreover, polyphenylenes, having in the molecule a halogen or a similar substituent, can be introduced into the macromolecular phosphine groups — $PR_2$ — using known processes, so that polyphenylene also functions effectively as an aromatic substituent in phosphine ligants. The resulting catalysts are polymeric analogs of phosphine complexes of transistion metals, as is desired.

A method in accordance with the invention for forming the above polyphenylene complex for use as a catalyst illustratively involves the steps of reacting a halogen compound of a metal selected from the group consisting of palladium, platinum, rhodium and ruthenium with polyphenylene of a specific weight of 1.000 – 3.000 in an organic solvent at a temperature of 60° – 120°C, and then applying a reducing agent to the obtained complex.

BRIEF DESCRIPTION OF THE DRAWING

An example of the application of the invention is described later in connection with the appended drawing, which shows in the form of curves the dependence of the catalytic activity of a polyphenylene-rhodium catalyst on the metal/polyphenylene ratio.

DESCRIPTION AND EXAMPLES

The polyphenylenes contemplated by the invention for use in the synthesis of π-complexes and analogs thereof are very inexpensive and accessible materials. In general, they may be manufactured by polycyclotrimerization of p-diethynilbenzene or from ketals or acetals by acetylene substitution of benzene. The copolymerization of diethynilbenzene with different derivatives of acetylene permits the introduction, into the polyphenylenes, of different functional groups to modify the properties of the polyphenylenes. This proves to be important when using polyphenylenes as ligants in catalytic systems.

In order to produce the inventive catalyst using such polyphenylenes, a halogen compound of palladium, platinum, rhodium or ruthenium, advantageously dichloro(ethylene)palladium complex, dichloro(ethylene)platinum complex, rhodium trichloride or ruthenium trichloride, is reacted with polyphenylene of a molecular specific weight of 1.000 to 3.000 in an organic solvent, advantageously dimethylformamide at a temperature of 60°–120°C (advantageously 80°C). The resulting compound is then reduced by a reduction agent selected, e.g. from the group consisting of formic acid, a hydrides complex, hydrogen, a naphthalene-sodium mixture, an organic anion-radical and sodium tetrahydroborate.

Two types of polymers can be employed as polyphenylenes, such polymers being obtained by polycyclotrimerization of p-diethinylbenzene. A difference between these two types is that the first contains unreacted triple C—C-bonds, while in the second case these bonds are eliminated by oxidation of the triple bond and by a following decarboxylation of the oxidation products. From the point of view of catalytic properties involving complexes of transistion metals with these types of polyphenylenes, there is no difference between them; therefore, the activity of the catalysts according to the invention is demonstrated by examples of complexes formed on polymeric supporting bases of the first type only. Polyphenylenes of a molecular specific weight of 1000 to 3000 can be most advantageously used for this purpose.

The polyphenylene is deposited on the transition metal by commonly used methods for obtaining π-complexes of transition metals. As reducing agents, different metals and different types of complexes, alcohols, molecular hydrogene, sodium borohydride, lithiumaluminiumhydride, organic anion-radicals and similar constituents can be used.

As shown in the drawing, the catalytic activity of polyphenylene catalysts (illustratively polyphenylene-rhodium catalysts) depends in a high degree on the relative amount of metal deposited on the macromolecule of polyphenylene. Such activity is manifested in the drawing as the percentage yield of isomer (curve 1) and olefin (curve 2) during the isomerization and hydrogenation of 1-octene. It can be proven that the maximum catalytic activity for rhodium catalysts occurs with a ratio of one atom of metal to 20 to 25 benzene cores. The amount of metal deposited on the polyphenylene depends on the starting concentration of the salt or of the complex of the transition metal deposited on the polyphenylene.

The polyphenylene catalysts of palladium, ruthonium and rhodium are active also for hydrogenation and isomerization of olefins in the presence of formic acid.

The type of catalyst, the concentration of formic acid, and the time and temperature of the reaction influence the yield of reaction products. It has been found that in the absence of the solvent an isomerization of olefins proceeds only in the presence of these catalysts.

The most active of the group of polyphenylene catalysts are rhodium compounds employed for hydrogenation and isomerization of olefins by molecular hydrogene and formic acid. In the presence of these compounds, the hydrogenation of the final olefins to parafins proceeds easily, whereby the catalyst can, after separation of the product, be re-used repeatedly without loss of activity. Such rhodium polyphenylene catalysts are also very effective for hydrosilylation.

The catalytic activity of the polyphenylene catalysts does not significantly change even upon exposure to dry or wet air for several months, and they are therefore very suitable for practical use.

A further substantial advantage is the fact that complexes of transition metals metals with polyphenylenes can be used both in a soluble and in an insoluble form, depending on the molecular specific weight of the supporting material. Also, both homogeneous and heterogeneous processes can proceed in their presence depending on the requirements of the particular application.

The hydrosilylation of acrylonitrile by trichlorsilan in the presence of rhodium polyphenylenes proceeds to a $\beta$-isomer $Cl_3SiCH_2CH_2CN$. This represents the first case where a $\beta$-product has been obtained on catalysts containing a transition metal. The hydrosilylation proceeds both in the presence of a solvent (such as benzene, tetrahydrofurane or the like) and in the absence of the solvent.

Examples of application of the invention are as follows:

EXAMPLE 1 a. 3.94 g polyphenylene of a molecular specific weight of 2000 in 100 ml of dimethylformamide was introduced in an argon atmosphere into a three-necked bottle that was provided with stirring means, a dropping funnel and a reflux cooler. The solution was heated to 80°C under intensive stirring, and a solution of 2 g $RhCl_3.3H_2O$ in 100 ml of dimethylformamide was added drop by drop.

The heating proceeded thereafter for 2 hours at 80°C. The reaction mixture was thereafter cooled to room temperature, after which 2.0 g sodium borhydride in 200 ml of water was added drop by drop. A light yellow precipitate was formed in the course of this reduction, and was separated out by a centrifuge and dried in an desiccater under vacuum.

The catalyst contained 4.22% of rhodium, and was soluble in dimethylformamide and benzene and insoluble in alcohol and ether.

b. To a solution of 3.96 g polyphenylene in 100 ml of dimethylformamide, a solution of 2.6 g $RhCl_3.H_2O$ in dimethylacetamide was introduced drop by drop at a temperature of 80°C. The reaction mixture was heated for 2 hours at the same temperature, after which the liquid was cooled. After reaching room temperature, the substance was reduced by means of an aqueous solution of 2 g $NaBH_4$ in 200 ml of water. The thus-obtained product was filtered, rinsed by means of ethyl alcohol and dried under vacuum. The final product contained 5.1% by weight of rhodium.

c. To a solution of 3.96 g polyphenylene in 100 ml of dimethylformamide, a solution of 2.6 g $RhCl_3.H_2O$ in 100 ml of dimethylformamide was introduced at a temperature of 80°C. The reaction mixture was heated for 2 hours while the temperature was raised to 120°C. Into the reaction mixture was introduced a stream of hydrogen for 6 hours. The reaction product was decanted by means of 200 ml of water, after which the substance was filtered, rinsed by means of ethyl alcohol and dried under vacuum. The product obtained contained 4.3% by weight of rhodium.

EXAMPLE 2

Into a three-necked bottle provided with stirring means, a drop funnel and a reflux cooler, a solution of 3.96 g of polyphenylene of a molecular specific weight of 3000 in 100 ml of dimethylformamide was introduced in an argon atmosphere. After heating the solution to 80°C, 2.25 g of $RuCl_3.H_2O$ in 100 ml of dimethylformamide was added drop by drop under intensive stirring. After addition of this solution, the reaction mixture was further heated for 2 hours to 80°C, and after cooling to room temperature, 2.0 g of sodium borhydride in 200 ml of water is added. A yellow precipitate was formed which was filtered, carefully washed by water and alcohol and dried under vacuum in an exsiccator. The catalyst contained 5.31% of ruthenium.

EXAMPLE 3

2 g of the catalyst prepared according to Example 2 was dissolved in tetrahydrofurane in the presence of argon. Under intensive stirring a napthalene-sodium solution prepared from 1.15 g sodium and 6 g napthalene in 30 ml of tetrahydrofurane was added. After heating for 4 hours, ethyl alcohol was added to the reaction mixture drop by drop until all the napthalene-sodium was decomposed. The solution was then filtered and evaporated, leaving a precipitate which was filtered, washed by a mixture of ethanolbenzene (5:1) and dried under vacuum.

The catalyst contained 6.2% ruthenium.

EXAMPLE 4

0.16 g (ethylene) $PdCl_2$, 0.8 g polyphenylene of a molecular specific weight of 1300, and 100 ml of benzene was introduced into a reaction vessel and left standing for 24 hours. The reaction mixture was thereafter heated for 2 hours to 60°C. The obtained product was precipitated by ethanol and filtered. The precipitate was stirred for some time with an acetonitrile solution of LiCl to remove the $PdCl_2$. The precipitate was thereafter washed with water and ethanol and dried under vacuum. The catalyst contained 4.88% palladium.

EXAMPLE 5

The test of Example 4 was repeated with the difference that, instead of 0.16 g (ethylene) $PdCl_2$, the same amount of (ethylene) $PtCl_2$ was used. The thus-prepared catalyst contained 3.60% platinum.

EXAMPLE 6 a. 7.0 g of 1-octene and 0.4 g of a catalyst prepared according to Example 1(a) was introduced into a reaction vessel, and the reaction mixture was mixed at 70°C in a hydrogen atmosphere. Within 3 hours 1.5 liters of gas was absorbed. The solution was separated from the catalyst, and the yield of octene was significant. 7.0 g of 1-octene was then again added to the catalyst, and the reaction was repeated. n-octene was again obtained by a significant quantitative yield.

b. A mixture of 0.4 g polyphenylene-rhodium catalyst containing 0.5% by weight of rhodium, 10 ml of formic acid and 10 ml of 1-octene was heated for 3 hours at a temperature of 80°C. The thus-obtained substance contained a mixture of 2-octene, 3-octene and 4-octene isomers. The yield was 16%.

c. A mixture of 0.4 g polyphenylene-rhodium catalyst containing 20% by weight of rhodium, 10 ml of formic acid and 10 ml of 1-octene was heated for 3 hours at a temperature of 80°C. The thus-obtained substance contained a mixture of 2-octene, 3-octene and 4-octene isomers. The yield this time was 26%.

EXAMPLE 7

These tests involved the reduction and isomerization of olefins of formic acid in the presence of rhodium-, ruthenium-, and palladium-polyphenylene catalysts.

a. 0.4 g rhodium-polyphenylene catalyst, 10 ml of formic acid and 10 ml of 1-octene were introduced into a reaction vessel and heated to 80°C for 3 hours. A mixture of 1-octene isomers was obtained in a 75% yield.

b. 0.4 g rhodium-polyphenylene catalyst, 10 ml of formic acid and 10 ml of 1-octene were introduced into a reaction vessel and heated to 80°C in a demethylformamide solution. 45% of octene and 28% of a mixture of isomers of octene were obtained.

c. 0.4 g ruthenium-polyphenylene catalyst, 10 ml of formic acid, 10 ml of 1-octene and 100 ml of dimethylformamide were introduced into a reaction vessel. The reaction mixture was heated to 80°C. Octene in a 75% yield was obtained.

d. 0.4 g palladium-polyphenylene catalyst, 10 ml of formic acid, 10 ml of 1-octene and 100 ml of dimethylformamide were introduced into a reaction vessel. The reaction mixture was heated to 80°C for 3 hours. A mixture of isomers was obtained in a 25% yield.

EXAMPLE 8

These tests involved the hydrosilylation of unsaturated compounds catalyzed by a rhodium-polyphenylene complex.

a. 400 g 1,3-butadiene, 420 g triethoxysilane and 2 g of a catalyst prepared according to Example 1 were introduced into a reaction vessel and heated to 100°C for 3 hours. After distillation, a reaction mixture of 538 g (95% of the theoretical amount) of $CH_3CH=CHCH_2Si(OC_2H_5)_3$ was obtained.

b. 500 g ethyldiethoxysilane, 510 g 1-heptene and 3 g of a catalyst prepared according to Example 1 were introduced into a reaction vessel. After heating the reaction mixture for 2 hours to 80°C, 585 g of ethylheptyldiethoxysilane (70% of the theoretical amount) were obtained by distillation.

c. 390 g vinylethylether, 600 g triethoxysilane, 3 g of a catalyst prepared according to Example 1 and 1000 ml of benzene were introduced into a reaction vessel and the mixture heated for 1.5 hours to boiling. After distillation, 786 g of $CH_3CH_2OCH_2CH_2Si(OC_2H_5)_3$ were obtained (90% of the theoretical amount).

d. 480 g vinyl acetate, 460 g triethylsilane and 3 g of a catalyst prepared according to Example 1 were introduced into a reaction vessel and the reaction mixture heated for 4 hours from 60° to 140°C 646 g of $CH_3COOCH_2CH_2Si(C_2H_5)_3$ were obtained by distillation in a vacuum.

Further examples, involving hydrogenation and isomerization of 1-heptane, are given in Tables 1 and 2 below.

TABLE 1

INFLUENCE OF THE AMOUNT OF FORMIC ACID PER MOL ON THE CATALYTIC ACTIVITY OF A RHODIUM-POLYPHENYLENE CATALYST FOR HYDROGENATION AND ISOMERIZATION OF 1-HEPTENE

Reaction conditions: 3 hours, 0.4 g of the catalyst, 7.0 g 1-heptene, 100 ml dimethylformamide.

| HCOOH (mol/mol) | Yield in mol% at 60°C n-heptane | heptenes(2,3) | Yield in mol% at 80°C n-heptane | heptene(2,3) |
|---|---|---|---|---|
| 1 | 0.4 | 7.5 | 18.7 | 53.2 |
| 2 | 0 | 11.5 | 15.0 | 58.2 |
| 3 | 0 | 13.0 | 7.9 | 60.4 |
| 4 | 0 | 18.0 | 0 | 64.3 |

TABLE 2

INFLUENCE OF AGEING OF A RHODIUM-POLYPHENYLENE CATALYST ON ITS CATALYTIC ACTIVITY DURING HYDROGENATION AND ISOMERIZATION OF 1-HEPTENE

Reaction conditions: 3 hours, 0.1 g HCOOH, 0.04 g of the catalyst, 0.7 g 1-heptene, 1 ml dimethylformamide.

| Ageing time days | Yield in mol% n-heptane | (2,3)heptenes |
|---|---|---|
| 15 | 45.1 | 28.9 |
| 30 | 45.0 | 28.6 |
| 45 | 45.0 | 28.8 |
| 60 | 44.8 | 28.5 |
| 90 | 44.8 | 28.5 |

In the foregoing, illustrative embodiments of the catalyst in accordance with the invention and examples of their method of preparation, have been described. Many variations and modifications will now occur to those skilled in the art. It is accordingly desired that the scope of the appended claims not be limited to the specific disclosure herein contained.

What is claimed is:

1. A catalyst for hydrogenation, isomerization and hydrolization of alkenes having from 2-16 atoms of carbon, said catalyst comprising a transition metal selected from the group consisting of palladium, platinum, rhodium and ruthenium complexed with polyphenylene having a molecular weight in excess of 1000, said metal being present in an amount ranging from 0.5 - 20 percent, by weight, based upon the weight of the catalyst.

2. A method of preparing a catalyst for hydrogenation, isomerization and hydrolyzation of alkenes having from 2–16 atoms of carbon in their molecules, comprising the steps of reacting a halogen compound of a metal selected from the group consisting of palladium, platinum, rhodium and ruthenium with polyphenylene of a specific weight of 1000–3000 in an organic solvent at a temperature within the range of 60°–120°C, so resulting in the formation of a polyphenylene complex, and effecting the reduction of the resultant composition by reaction with a reducing agent to yield a catalyst having from 0.5 – 20 percent, by weight, of said metal.

3. A method as defined in claim 2, in which the halogen compounds are selected from the group consisting of dichloro(ethylene) palladium complex, a dichloro(ethylene) platinum complex, rhodium trichloride, and ruthenium trichloride.

4. A method as defined in claim 2, in which the reducing agent is selected from the group consisting of formic acid, hydrogen, a napthalene-sodium mixture, and sodium tetrahydroborate.

5. A method as defined in claim 2, in which the organic solvent is dimethylformamide.

6. A method as defined in claim 2, in which the reaction temperature is 80°C.

* * * * *